United States Patent
Yildirim et al.

(10) Patent No.: US 10,999,530 B1
(45) Date of Patent: May 4, 2021

(54) TECHNIQUES FOR GENERATING TIME-SERIES IMAGES OF CHANGES IN PERSONAL APPEARANCE

(71) Applicant: L'Oreal, Paris (FR)

(72) Inventors: Ozgur Emek Yildirim, Bellevue, WA (US); Mehdi Doumi, North Plainfield, NJ (US); Geoffrey F. Deane, Bellevue, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/696,871

(22) Filed: Nov. 26, 2019

(51) Int. Cl.
| | | |
|---|---|---|
| *H04N 5/93* | (2006.01) | |
| *H04N 5/262* | (2006.01) | |
| *G06T 5/00* | (2006.01) | |
| *H04N 5/265* | (2006.01) | |
| *G06K 9/00* | (2006.01) | |
| *G11B 27/031* | (2006.01) | |
| *G06T 7/33* | (2017.01) | |

(52) U.S. Cl.
CPC ....... *H04N 5/2625* (2013.01); *G06K 9/00268* (2013.01); *G06T 5/002* (2013.01); *G06T 5/007* (2013.01); *G06T 7/33* (2017.01); *G11B 27/031* (2013.01); *H04N 5/265* (2013.01); *H04N 5/2628* (2013.01); *G06T 2207/10016* (2013.01); *G06T 2207/20132* (2013.01); *G06T 2207/20221* (2013.01); *G06T 2207/30088* (2013.01); *G06T 2207/30201* (2013.01)

(58) Field of Classification Search
CPC . G06T 2207/10016; G06T 2207/20104; G06T 5/00; H04N 5/2621; G06K 9/00677
USPC .......... 386/278, 281, 290, 226, 223
See application file for complete search history.

(56) References Cited

U.S. PATENT DOCUMENTS

| | | |
|---|---|---|
| 8,248,491 B2 | 8/2012 | On |
| 9,451,165 B2 | 9/2016 | Okuhira et al. |
| 10,068,363 B2 * | 9/2018 | Laaksonen ............... G06K 9/46 |

(Continued)

FOREIGN PATENT DOCUMENTS

| | | |
|---|---|---|
| EP | 2 759 981 A1 | 7/2014 |
| JP | 2003 223648 A | 8/2003 |

OTHER PUBLICATIONS

International Search Report and Written Opinion dated Mar. 16, 2021, issued in corresponding International Application No. PCT/US2020/061831, filed Nov. 23, 2020, 16 pages.

(Continued)

*Primary Examiner* — Robert Chevalier
(74) *Attorney, Agent, or Firm* — Christensen O'Connor Johnson Kindness PLLC (57) ABSTRACT

A computer system creates time lapse video of a live subject to help assess effects of skin treatments, use of cosmetics, or personal care routines over time. In one aspect, the computer system obtains a set of digital source images (e.g., from video or a series of still images) of a region of interest of a live subject (e.g., the face of the live subject or a portion thereof) captured in a first time period; normalizes the set of digital source images; obtains a first representative image that includes the region of interest by synthesizing or selecting it from the set of digital source images; and combines the first representative image with additional representative images from other time periods to form a time lapse video of the region of interest of the live subject.

24 Claims, 5 Drawing Sheets

(56) References Cited

U.S. PATENT DOCUMENTS

2003/0063102 A1     4/2003    Rubinstenn et al.
2018/0015300 A1     1/2018    Hamid

OTHER PUBLICATIONS

J. Keller, "The Adaption to My Generation (a daily photo project)", https://jk-keller.com/o_o/daily_photo. retrieved from the Internet on Mar. 3, 2021, Oct. 2014, pp. 1-5.

G. Holtzer, "10 Best Time-Lapse Apps for Photographers 2021", https://expertphotography.com/time-lap se-photography-apps/, retrieved from the Internet on Mar. 3, 2021, pp. 1-12.

S. Madan et al, "Multimodal and time-lapse skin registration", Skin Research and Technology, Vol . 21, No. 3, Nov. 18 2014, pp. 319-326.

Pro-Lapse: "Can I turn a video into a time-lapse?", https://www.pro-lapse.com/can-i-turn-a-video-into-a-time-lapse/, retrieved from the Internet on Mar. 4, 2021, pp. 1-4.

\* cited by examiner

TECHNIQUES FOR GENERATING TIME-SERIES IMAGES OF CHANGES IN PERSONAL APPEARANCE

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer system performs a method of creating time lapse video of a live subject, e.g., to help assess effects of skin treatments, use of cosmetics, or personal care routines over time. The method comprises obtaining, by a computing device, a set of digital source images (e.g., from video or a series of still images) of a region of interest of a live subject (e.g., the face of the live subject or a portion thereof), wherein the set of digital source images is captured in a first time period; obtaining a first representative image that includes the region of interest by synthesizing or selecting the first representative image from the set of digital source images, wherein the first representative image is associated with the first time period; and combining the first representative image with one or more additional representative images that include the region of interest of the live subject to form a time lapse video of the region of interest of the live subject, wherein the one or more additional representative images are associated with one or more additional time periods.

In an embodiment, obtaining the first representative image that includes the region of interest includes synthesizing the first representative image by selecting portions of two more of the digital source images and combining the selected portions in a composite image.

In an embodiment, the set of digital source images comprises images taken from different angles. In an embodiment, obtaining the first representative image that includes the region of interest includes synthesizing the first representative image by selecting portions of the images taken from different angles and forming a composite image comprising the selected portions.

In an embodiment, the method further comprises identifying one or more feature points (e.g., one or more facial features of the live subject) in each of the digital source images.

In an embodiment, the method further comprises normalizing the set of digital source images. In an embodiment, the synthesizing or selecting of the first representative image includes synthesizing or selecting from the set of normalized digital source images. In an embodiment, normalizing the set of digital source images comprises one or more of performing noise reduction in one or more of the digital source images; adjusting the orientation of one or more of the digital source images; cropping one or more of the digital source images; adjusting brightness of one or more of the digital source images; or adjusting contrast of one or more of the digital source images.

In an embodiment, the method further comprises causing the time-lapse video to be displayed, e.g., on a mobile computing device at the request of a user.

DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein.

DETAILED DESCRIPTION

Within the cosmetics and personal care industries, a known technique for measuring differences in personal appearance over time is to capture consistently posed and lighted images over time at designated intervals. In a simple example, consistently posed and lighted images are captured to show differences between a consumer's appearance before and after an event, such as the consumer's use of a particular personal care device or product. The consistent poses and lighting allow images to be analyzed to detect differences in appearance related to, e.g., use of a particular personal care device or product.

However, it is very difficult for consumers working at home to capture consistently posed and lighted images. The technical skill and lighting equipment required for capturing such images are not attainable for the average consumer. On the other hand, if images or video of the consumer are captured in uncontrolled environments (e.g., without regard to lighting, maintaining a consistent pose, etc.), those images cannot currently be used to reliably track progress in personal care routines due to technical difficulties of processing images from uncontrolled environments. What is desired are techniques that can overcome these technical limitations in order to accurately track progress of skin treatments, use of cosmetics, or personal care routines without the use of professional photographers or professional photography equipment.

In some embodiments of the present disclosure, a computer system produces time series images to accurately illustrate gradual changes in personal appearance, such as changes in skin conditions over time. The time series images are assembled from images captured without the need for professional photographers or professional photography equipment. In an embodiment, a user captures video or a series of still images of themselves at periodic intervals (e.g., once per day) which, after pre-processing, can be used to generate output such as a time-morph video to demonstrate changes over time. In a cosmetics or personal care context, such videos are used to demonstrate progress made in personal care (e.g., improvements in skin condition, skin color, skin texture, hair condition, etc.) Such videos can be shared with others (e.g., via social media platforms or directly from one computing device to another).

In an embodiment, a user captures a large number of source images (e.g., 10, 20, hundreds, etc.) of a region of interest of a live subject (e.g., the user's face or a portion of the user's face), which may be taken at different time instances in different environments, from a variety of angles in a range of possible lighting conditions. The images are normalized to an objective baseline, to allow accurate comparisons and illustration of changes over time. The normalization can be used to reduce effects of variations in lighting/exposure, orientation, camera jitter, lens condition, and the like. These images are post-processed to obtain a representative image, which may include selecting an image from among the source images or using portions of two or more source images to synthesize a new image (e.g., by averaging, compositing, or otherwise combining image data from the source images). In an embodiment, a representative image is associated with a time period in which the corresponding source images are captured (e.g., weekly, daily, twice daily, etc.).

In an embodiment, the synthesized images are combined to form a time series morph video that depicts physiological or other changes in appearance over time, such as making wrinkles or blemishes less apparent, rejuvenation of skin, improvements in skin tone, and the like. By employing a consistent approach to how the representative image is processed for each time period, the variations of conditions in the synthesized images are much reduced relative to the variations that may be present in the source images. This allows for greater ease and accuracy in comparing the images to track changes in the consumer's appearance over time.

Figure 1:
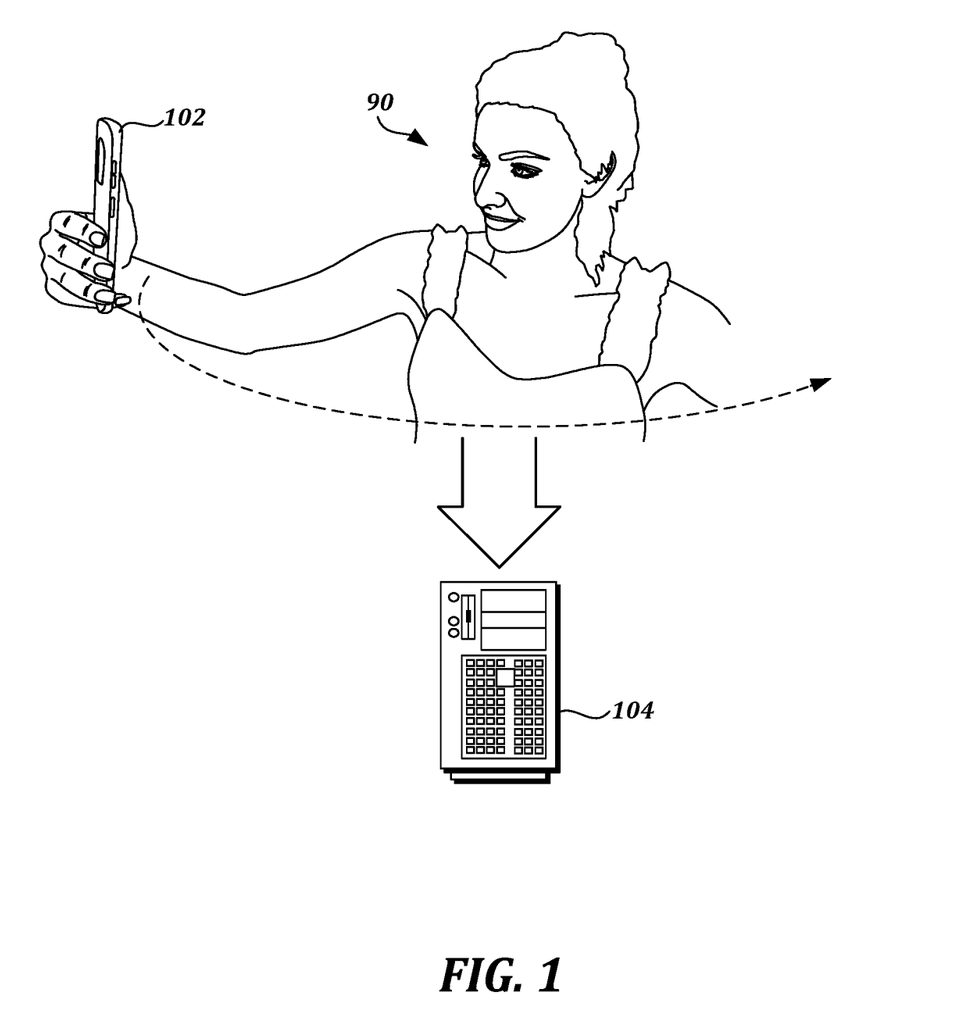
FIG. 1 is a schematic illustration of an example embodiment of a system that obtains images and generates time lapse video of a live subject according to various aspects of the present disclosure.

FIG. 1 is a schematic illustration of a non-limiting example embodiment of a system that obtains images and generates time lapse video according to various aspects of the present disclosure. As shown, a user 90 captures one or more digital source images of her face with a mobile computing device 102. The user 90 may be in any type of location, and therefore the lighting conditions and other environmental factors in which the image is captured may be unknown.

In some embodiments, the mobile computing device 102 captures and transmits a time series of images to a time-lapse video processing computer system 104. The images may be obtained from video or from a series of still images. Lighting conditions and viewing angles may differ among the captured source images. In an illustrative scenario, depicted in FIG. 1, the user 90 configures the mobile computing device 102 to capture video or still images using a front-facing camera (also known as a "selfie" camera), and moves the mobile computing device 102 in a semi-circular motion to capture images of a region of interest (e.g., the user's face or a portion thereof, such as the user's forehead, eyes, etc.) from different angles. In another embodiment, a camera (e.g., a front-facing camera of a laptop computer or other computing device) is maintained in a fixed position while the user turns her head in different directions to capture images of a region of interest from different angles.

By capturing images at different angles, the images provide a more complete representation of the region of interest. This may be useful for tracking progress on improving skin tone, reducing blemishes or acne lesions, or minimizing the appearance of wrinkles or "crow's feet," which may present themselves in different ways on different portions of the user's face or be more apparent when viewed from different angles. Further adjustments may be made during the image capture process, including electronic or optical image stabilization. In addition, post-processing techniques may be used to improve the utility of source images. For example, individual source images may be stitched into a panoramic image from multiple images in order to increase the effective field of view.

Figure 2:
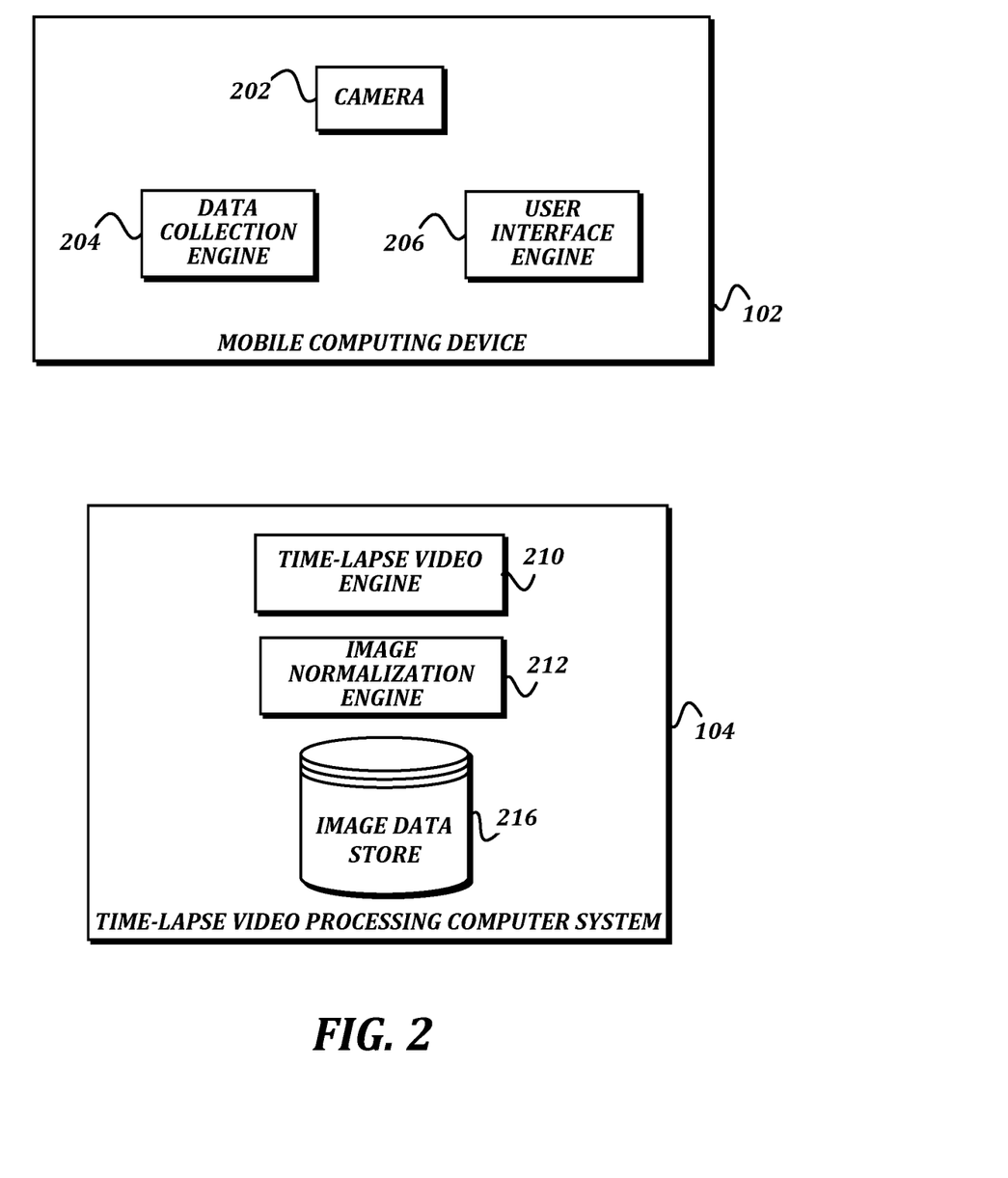
FIG. 2 is a block diagram that illustrates example embodiments of a mobile computing device and a time-lapse video processing computer system according to various aspects of the present disclosure.

FIG. 2 is a block diagram that illustrates non-limiting example embodiments of a mobile computing device and a time-lapse video processing computer system according to various aspects of the present disclosure. As discussed above, the mobile computing device 102 (a smartphone, a tablet computing device, a laptop computer, or another computing device) is used to capture still images or video of a user 90. The mobile computing device 102 transmits the video or still images to the time-lapse video processing computer system 104 (e.g., a desktop computing device, a server computing device, a cloud computing device, or another computing device or combination of computing devices), which generates time-lapse video of the user 90 or modifies an existing time-lapse video with new images from a current image capture session. The mobile computing device 102 and the computer system 104 may communicate using any suitable communication technology, such as wireless communication technologies including but not limited to Wi-Fi, Wi-MAX, Bluetooth, 2G, 3G, 4G, 5G, and LTE; or wired communication technologies including but not limited to Ethernet, FireWire, and USB. In some embodiments, the communication between the mobile computing device 102 and the computer system 104 may occur at least in part over the Internet.

In the illustrated embodiment, the mobile computing device 102 includes a camera 202, a data collection engine 204, and a user interface engine 206. The camera 202 is configured to capture digital source images for subsequent use in generating or modifying time-lapse video. In some embodiments, the mobile computing device 102 may include multiple cameras, including but not limited to a front-facing camera and a rear-facing camera. In some embodiments, the front-facing camera (that is, a camera located on a same face of the mobile computing device 102 as a display of the mobile computing device 102) is used as the camera 202 for capturing images. In other embodiments, a computing device is used in combination with an external digital camera to capture source images.

The data collection engine 204 is configured to use the camera 202 to capture images of the user 90. The user interface engine 206 is configured to present a user interface to the user 90. In some embodiments, the user interface includes a graphical user interface to assist a user in obtaining high-quality images, viewing tutorials that assist the user 90 in capturing high-quality images, viewing time-lapse video generated from the images, or the like. In an embodiment, the user interface provides guidance (e.g., in the form of visual guides such as arrows or targets, progress indicators, audio/haptic feedback, synthesized speech, etc.) to encourage a user to continue taking images or to take images from particular angles in order to ensure that sufficient data is collected to synthesize a representative image for a particular time instance. By doing so, the user interface engine 206 helps to ensure that representative images are of sufficient quality and consistency to be accurately compared with other synthesized images captured at different time instances.

In the illustrated embodiment, the computer system 104 includes a time-lapse video engine 210 and an image normalization engine 212. As shown, the computer system 104 also includes an image data store 216, in which captured digital source images can be stored until they are needed for further processing. The time-lapse video engine 210 is configured to generate time-lapse video based on captured source images.

In an embodiment, a set of digital source images is captured by the mobile computing device 102 in a first time period and transmitted by the mobile computing device 102 to the computer system 104. In an embodiment, the user interface engine 206 provides special instructions or image capture tools for capturing a particular region of interest (e.g., eyes, forehead, neck, etc.).

In an illustrative scenario, the mobile computing device 102 (or some other computing device) controls a digital video camera to capture source images as video frames. The captured video is provided as input to a feature detection engine, which detects and tracks facial features over time in the video. The video need not be of a long duration to be effective. For example, the video may capture sufficient feature data over a few seconds to detect and accurately represent facial features. In an embodiment, the video camera remains in a fixed location as the user turns her head in different directions to face the camera at different angles. Taken together, the frames of the video allow facial features to be captured in sufficient detail for making useful comparisons.

In some embodiments, the same features or similar features are detected and tracked in a similar way in subsequent videos, in order to maintain consistency and track changes in facial features over time. In an embodiment, the facial features are parameterized (e.g., using color values, light values, of pixels corresponding to the detected features) to assist in comparisons of features captured at different time instances. For example, comparisons to measure changes in appearance of wrinkles or blemishes over time may involve detecting facial features associated with known wrinkle/blemish locations at different time instances and determining light or color values in these areas to allow comparisons over time. These changes can be represented in time-lapse videos in accordance with embodiments described herein.

In some embodiments, the time-lapse video engine 210 obtains a representative image from the set of digital source images, associating that representative image with the first time period. In an embodiment, feature points are identified in the source images to assist in obtaining the representative images. In an embodiment, the time-lapse video engine identifies feature points in source images as part of the process of obtaining a representative image, such as by selecting an image in which key feature points are of highest quality, averaging image regions containing such feature points to form a composite image. Alternatively, a representative image can be obtained in some other way.

The time-lapse video engine 210 combines that representative image with additional representative images from earlier time periods to form a time-lapse video segment. The time-lapse video segment can be annotated with additional features that allow progress to be more easily seen by a user, such as highlighting or outlining areas of interest (e.g., wrinkles, eyelashes, etc.) such that changes in those areas of interest over time can be more easily seen.

In an illustrative scenario, a user applies an eyelash serum onto her eyelashes twice daily for thirty days. Each day, the user captures a series of images of her eyes with a mobile computing device 102 and uploads those images to the time-lapse video processing computer system 104. In an embodiment, such images are captured as video or in a still-image burst mode, in which a series of still images are captured (e.g., with a single button push) at a predefined rate, e.g., 10 images per second. In an embodiment, the user interface engine 206 provides special instructions for capturing eyelash images, such as by instructing the user to hold the camera close to the eye area and to take one set of images with open eyes and one set of images with closed eyes. The time-lapse video engine 210 obtains a representative image from the set of digital source images, by selecting one or more high-quality (e.g., good lighting, limited blurring) open-eye and closed-eye images and averaging or otherwise combining portions of these images to form a composite image as the representative image. In an embodiment, the representative image undergoes further processing by identifying feature points in the image (e.g., eyes, eyebrows, eyelids, etc.). In an embodiment, such feature points are identified using computer vision techniques such as edge detection, corner detection, and the like, and are tracked across frames of a time-lapse video. These feature points can be used in further processing to assist the user in tracking progress. In this example, feature points can be used to identify the eyelash area and draw a bounding box around the perimeter of the eyelashes. When these bounding boxes are displayed in frames of a time-lapse video, comparisons of the eyelash area in frames of the time-lapse video show the user's progress in growing thicker, longer eyelashes.

In some embodiments, the image normalization engine 212 is configured to pre-process images before they are provided to the time-lapse video engine 210 in order to improve the quality of the time-lapse video. Image normalization of source images may include, for example, performing noise reduction or filtering; adjusting orientation; cropping; adjusting brightness/exposure; adjusting contrast; adjusting contrast. An illustrative image normalization process is described below with reference to FIG. 4.

Many alternatives to the arrangements and usage scenarios depicted in FIGS. 1 and 2 are possible. For example, although FIG. 2 illustrates various components as being provided by the mobile computing device 102 or the computer system 104, in some embodiments, the arrangement or functionality of the components may be different. For example, in some embodiments, the time-lapse video engine 210, the image normalization engine 212, and the image data store 216 may be present on the mobile computing device 102 so that the mobile computing device 102 can generate time-lapse video without transmitting the images to the computer system 104. In this regard, all of the components illustrated in FIG. 2 may be provided by a single computing device. As yet another example, in some embodiments multiple computing devices work together to provide the components that are depicted in FIG. 2 as being provided by the computer system 104.

Figure 3:
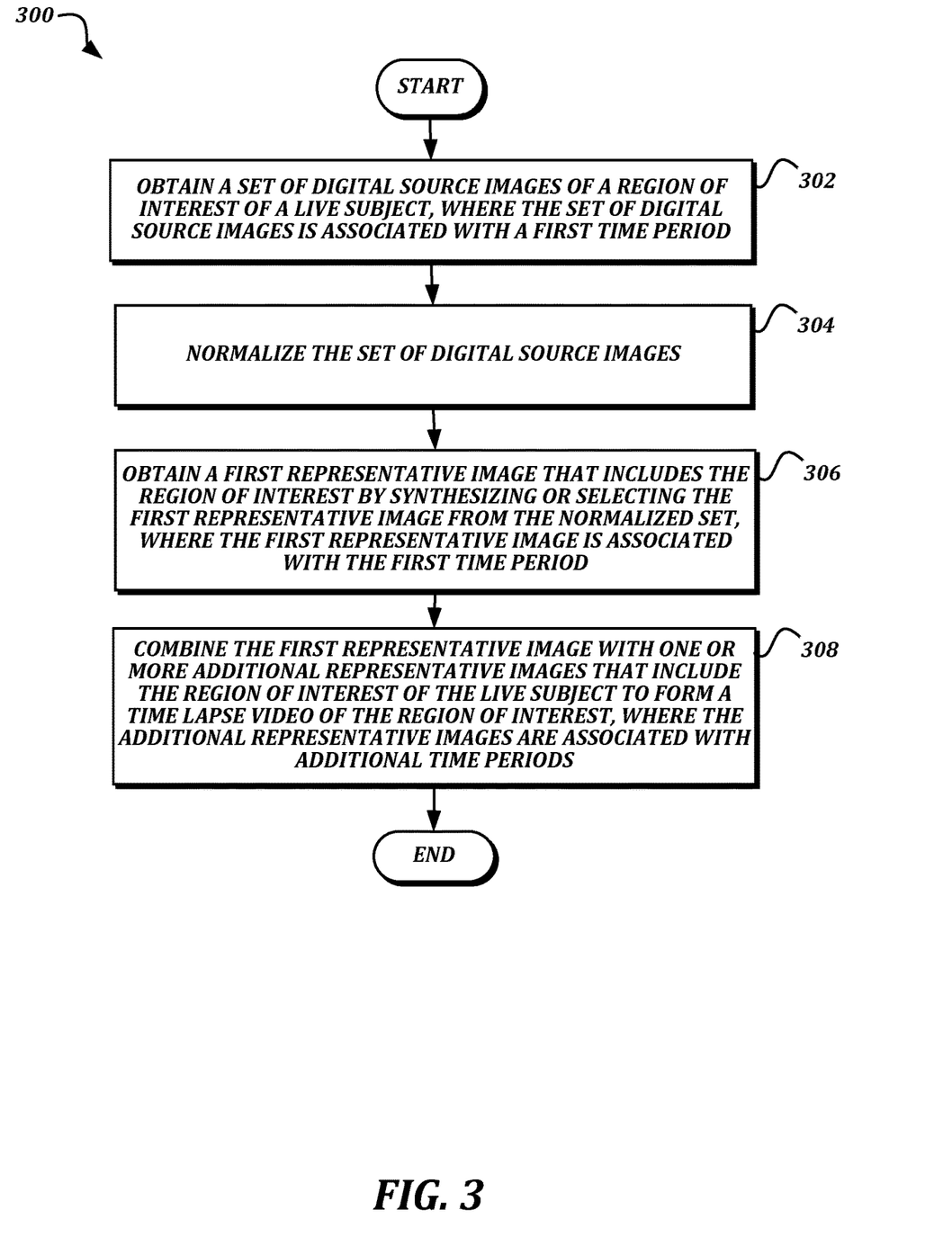
FIG. 3 is a flowchart that illustrates a non-limiting example embodiment of a method of generating a time lapse video of a region of interest of a live subject according to various aspects of the present disclosure.

FIG. 3 is a flowchart that illustrates a non-limiting example embodiment of a method 300 of generating a time lapse video of a region of interest of a live subject according to various aspects of the present disclosure. The method 300 is performed by a computer system including one or more computing devices. In an embodiment, the method 300 is performed by time-lapse video processing computer system 104. Alternatively, the method 300 is performed by some other computer system.

At block 302, a computer system obtains a set of digital source images (e.g., video or still images) of a region of interest of a live subject (e.g., the face of the live subject or portion of the face). In an embodiment, the computer system obtains the set of digital source images by receiving them from a client computing device that captured the set of digital source images, such as the mobile computing device 102, or by retrieving them from some other location. Alternatively, the computer system may obtain the set of digital source images by capturing them directly. The set of digital source images is captured in a first time period (e.g., by a client computing device such as the mobile computing device 102, or by some other computing device). In an embodiment, the set of digital source images is captured at different angles, in different lighting conditions, or with other variations.

At block 304, the computer system normalizes the set of digital source images. In an embodiment, the normalizing function includes one or more of performing noise reduction in one or more of the digital source images; adjusting the orientation of one or more of the digital source images; cropping one or more of the digital source images; adjusting brightness of one or more of the digital source images; or adjusting contrast of one or more of the digital source images, a combination of two or more of these normalization techniques, or other normalization techniques.

At block 306, the computer system obtains a first representative image that includes the region of interest by synthesizing or selecting the first representative image from the normalized set of digital source images. The first representative image is associated with the first time period. In an embodiment, obtaining the first representative image includes synthesizing the first representative image by selecting portions of two more of the normalized digital source images and combining the selected portions in a composite image. In an embodiment, the digital source images are taken from different angles, and the computer system synthesizes the first representative image by selecting portions of the images taken from different angles and forming a composite image that includes the selected portions or is derived from the selected portions.

At block 308, the computer system combines the first representative image with one or more additional representative images that include the region of interest of the live subject to form a time lapse video of the region of interest of the live subject. The one or more additional representative images are associated with one or more additional time periods. In an embodiment, the computer system causes the time-lapse video to be displayed or facilitates display of the time-lapse video, such as by transmitting the time-lapse video to a client computing device in response to a request received from the client computing device.

Many alternatives to the process depicted in FIG. 3 are possible. For example, in some embodiments normalization is performed at some other time or performed by some other computing system or device, such as during an image capture phase at a client computing device. In this regard, normalization is omitted from the method 300 in some embodiments.

Figure 4:
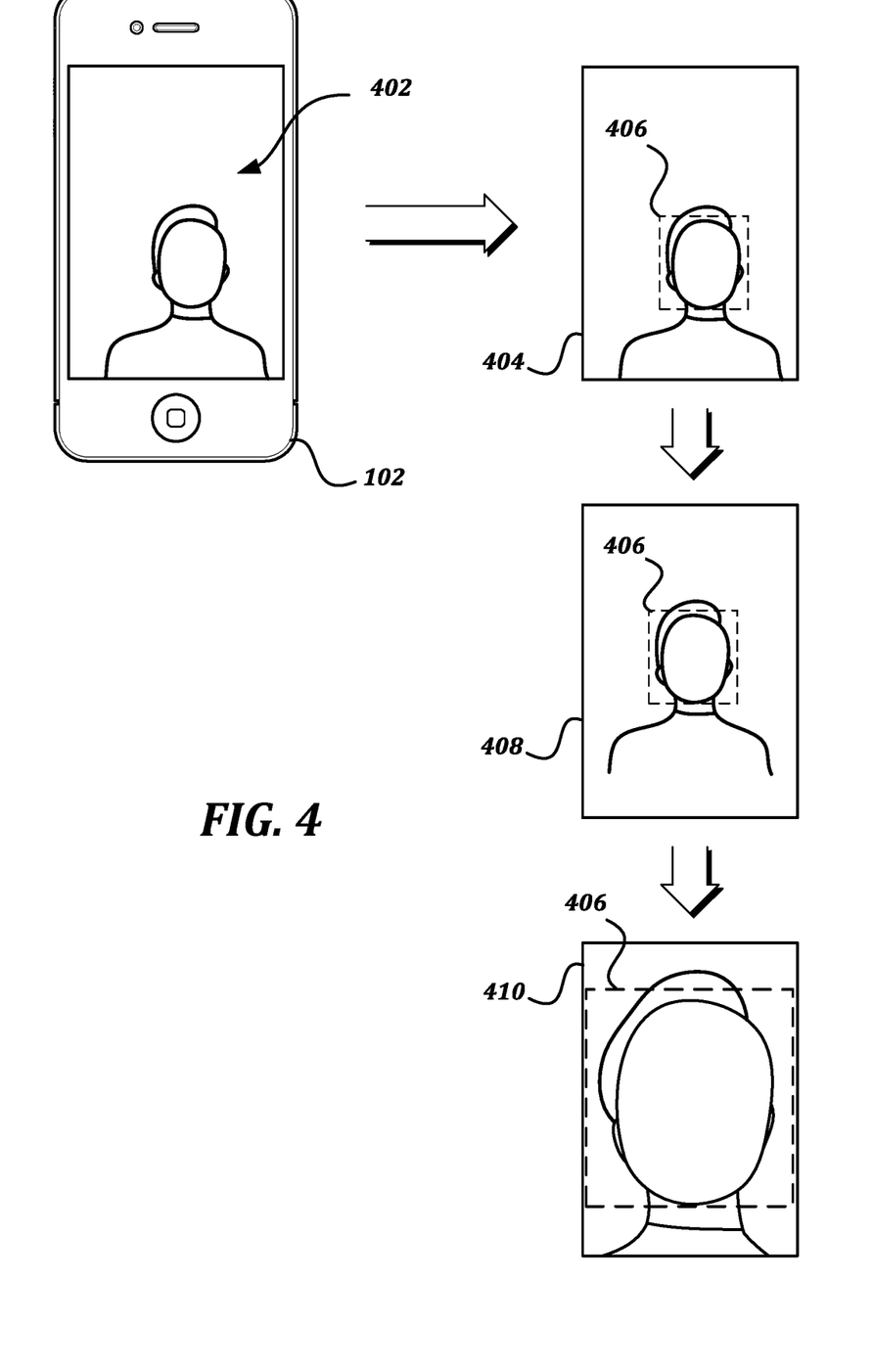
FIG. 4 is a schematic drawing that illustrates a non-limiting example embodiment of normalization of an image that includes a face according to various aspects of the present disclosure.

FIG. 4 is a schematic drawing that illustrates a non-limiting example embodiment of normalization of an image that includes a face of a live subject, according to various aspects of the present disclosure. As shown, the mobile computing device 102 has captured an image 402 of a subject and is presenting the image 402 on a display device of the mobile computing device 102. The image 402 includes an off-center face that takes up only a small portion of the overall image 402. As such, it may be difficult to compare the image 402 to other images to identify a representative image for this time period. To allow for more accurate comparisons, it may be desirable to reduce the amount of the image that does not include the region of interest, such as by reducing non-face area in the image, and to place the region of interest in a consistent location.

In the example shown in FIG. 4, the region of interest is the subject's face. In this example, the image normalization engine 212 uses a feature detection algorithm (e.g., a specialized face detection algorithm) to detect the portion of the image 404 that depicts the face in a first normalization action 404. In an embodiment, the image normalization engine 212 uses the face detection algorithm to find a bounding box 406 that includes the face. In a second normalization action 408, the image normalization engine 212 alters the image 408 to center the bounding box 406 within the image 408. In a third normalization action 410, the image normalization engine 212 zooms in on the image 410 to cause the bounding box 406 to be as large as possible within the image 410. In other embodiments, the image normalization engine employs different normalization actions, such as cropping the image to the bounding box 406, reducing or increasing bit depth, undersampling or oversampling pixels of the image, or the like. Such normalization actions are used, in some embodiments, to match other images collected at different time instances, which may be taken with different cameras, at different viewing angles or orientations, or in different lighting conditions.

In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

Figure 5:
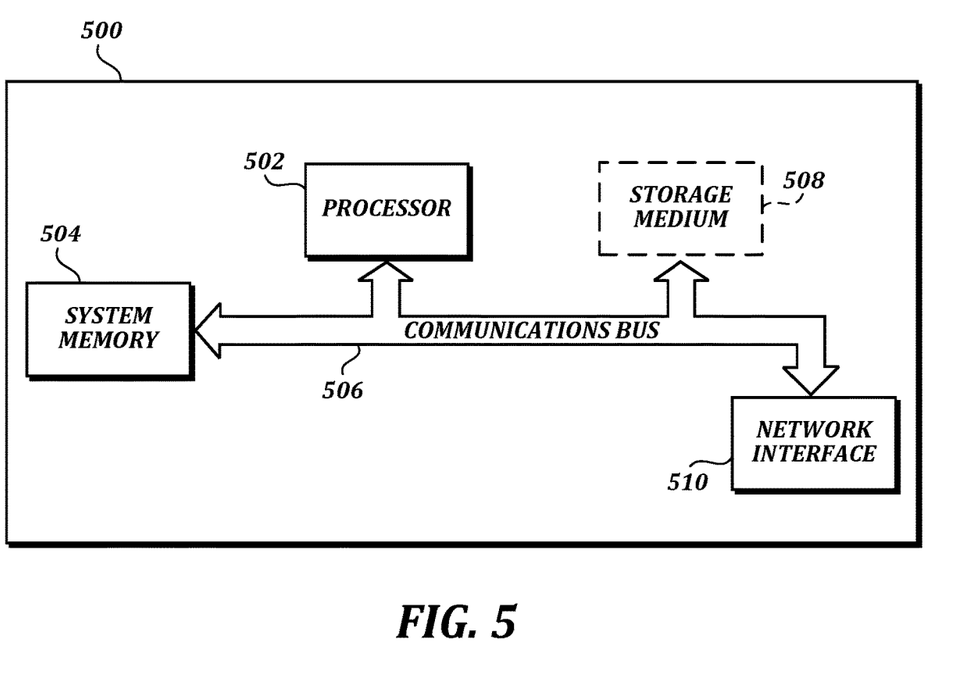
FIG. 5 is a block diagram that illustrates aspects of an exemplary computing device appropriate for use as a computing device of the present disclosure.

FIG. 5 is a block diagram that illustrates aspects of an exemplary computing device 500 appropriate for use as a computing device of the present disclosure. While multiple different types of computing devices were discussed above, the exemplary computing device 500 describes various elements that are common to many different types of computing devices. While FIG. 5 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 500 may be any one of any number of currently available or yet to be developed devices.

In its most basic configuration, the computing device 500 includes at least one processor 502 and a system memory 504 connected by a communication bus 506. Depending on the exact configuration and type of device, the system memory 504 may be volatile or nonvolatile memory, such as read only memory ("ROM"), random access memory ("RAM"), EEPROM, flash memory, or similar memory technology. Those of ordinary skill in the art and others will recognize that system memory 504 typically stores data and/or program modules that are immediately accessible to and/or currently being operated on by the processor 502. In this regard, the processor 502 may serve as a computational center of the computing device 500 by supporting the execution of instructions.

As further illustrated in FIG. 5, the computing device 500 may include a network interface 510 comprising one or more components for communicating with other devices over a network. Embodiments of the present disclosure may access basic services that utilize the network interface 510 to perform communications using common network protocols. The network interface 510 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 510 illustrated in FIG. 5 may represent one or more wireless interfaces or physical communication interfaces described and illustrated above with respect to particular components of the system 100.

In the exemplary embodiment depicted in FIG. 5, the computing device 500 also includes a storage medium 508. However, services may be accessed using a computing device that does not include means for persisting data to a local storage medium. Therefore, the storage medium 508 depicted in FIG. 5 is represented with a dashed line to indicate that the storage medium 508 is optional. In any event, the storage medium 508 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 504 and storage medium 508 depicted in FIG. 5 are merely examples of computer-readable media.

Suitable implementations of computing devices that include a processor 502, system memory 504, communication bus 506, storage medium 508, and network interface 510 are known and commercially available. For ease of illustration and because it is not important for an understanding of the claimed subject matter, FIG. 5 does not show some of the typical components of many computing devices. In this regard, the computing device 500 may include input devices, such as a keyboard, keypad, mouse, microphone, touch input device, touch screen, tablet, and/or the like. Such input devices may be coupled to the computing device 500 by wired or wireless connections including RF, infrared, serial, parallel, Bluetooth, Bluetooth low energy, USB, or other suitable connections protocols using wireless or physical connections. Similarly, the computing device 500 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of creating time lapse video of a live subject, the method comprising:
   obtaining, by a computing device, a set of digital source images of a region of interest of a live subject, wherein the set of digital source images is captured in a first time period;
   normalizing the set of digital source images;
   obtaining a first representative image that includes the region of interest by synthesizing or selecting the first representative image from the set of digital source images, wherein the first representative image is associated with the first time period, wherein the synthesizing or selecting of the first representative image includes synthesizing or selecting from the set of normalized digital source images; and
   combining the first representative image with one or more additional representative images that include the region of interest of the live subject to form a time lapse video of the region of interest of the live subject, wherein the one or more additional representative images are associated with one or more additional time periods.

2. The method of claim 1, wherein the region of interest comprises at least part of the face of the live subject.

3. The method of claim 1, wherein the set of digital source images of the region of interest comprises video of the region of interest.

4. The method of claim 1, wherein the set of digital source images comprises images taken from different angles.

5. The method of claim 1, wherein obtaining the first representative image that includes the region of interest includes synthesizing the first representative image by selecting portions of two more of the digital source images and combining the selected portions in a composite image.

6. The method of claim 1, wherein the set of digital source images comprises images taken from different angles, and wherein obtaining the first representative image that includes the region of interest includes synthesizing the first representative image by selecting portions of the images taken from different angles and forming a composite image comprising the selected portions.

7. The method of claim 1 further comprising identifying one or more feature points in each of the digital source images.

8. The method of claim 7, wherein the one or more feature points comprise one or more facial features of the live subject.

9. The method of claim 1, wherein normalizing the set of digital source images comprises one or more of:
   performing noise reduction in one or more of the digital source images;
   adjusting the orientation of one or more of the digital source images;
   cropping one or more of the digital source images;
   adjusting brightness of one or more of the digital source images; or adjusting contrast of one or more of the digital source images.

10. The method of claim 1 further comprising causing the time-lapse video to be displayed.

11. A computer system programmed to create time lapse video of a live subject, the computer system comprising at least one processor and memory, the memory having stored therein computer-executable instructions configured to cause the computer system to perform steps comprising:
  obtaining a set of digital source images of a region of interest of a live subject, wherein the set of digital source images is captured in a first time period, and wherein the region of interest comprises at least part of the face of the live subject;
  obtaining a first representative image that includes the region of interest by synthesizing or selecting the first representative image from the set of digital source images, wherein the first representative image is associated with the first time period; and
  combining the first representative image with one or more additional representative images that include the region of interest of the live subject to form a time lapse video of the region of interest of the live subject, wherein the one or more additional representative images are associated with one or more additional time periods.

12. The computer system of claim 11, wherein the set of digital source images of the region of interest comprises video of the region of interest.

13. The computer system of claim 11, wherein the set of digital source images comprises images taken from different angles.

14. The computer system of claim 11, wherein obtaining the first representative image that includes the region of interest includes synthesizing the first representative image by selecting portions of two more of the digital source images and combining the selected portions in a composite image.

15. The computer system of claim 11, wherein the computer-executable instructions are further configured to cause the computer system to perform steps comprising registering one or more feature points in each of the digital source images.

16. The computer system of claim 11,
  wherein the set of digital source images comprises one or more normalized digital source images, and wherein the synthesizing or selecting of the first representative image includes synthesizing or selecting from the one or more normalized digital source images.

17. The computer system of claim 16, wherein the one or more normalized digital source images are normalized using one or more of the following:
  performing noise reduction;
  adjusting orientation;
  cropping;
  adjusting brightness; or
  adjusting contrast.

18. A non-transitory computer-readable medium having stored thereon computer-executable instructions configured to cause a computer system to perform steps comprising:
  obtaining a set of digital source images of a region of interest of a live subject, wherein the set of digital source images is captured in a first time period, and wherein the region of interest comprises at least part of the face of the live subject;
  obtaining a first representative image that includes the region of interest by synthesizing or selecting the first representative image from the set of digital source images, wherein the first representative image is associated with the first time period; and
  combining the first representative image with one or more additional representative images that include the region of interest of the live subject to form a time lapse video of the region of interest of the live subject, wherein the one or more additional representative images are associated with one or more additional time periods.

19. The non-transitory computer-readable medium of claim 18, wherein the set of digital source images of the region of interest comprises video of the region of interest.

20. The non-transitory computer-readable medium of claim 18, wherein the set of digital source images comprises images taken from different angles.

21. The non-transitory computer-readable medium of claim 18, wherein obtaining the first representative image that includes the region of interest includes synthesizing the first representative image by selecting portions of two more of the digital source images and combining the selected portions in a composite image.

22. The non-transitory computer-readable medium of claim 18, wherein the computer-executable instructions are further configured to cause the computer system to perform steps comprising registering one or more feature points in each of the digital source images.

23. The non-transitory computer-readable medium of claim 18, wherein the set of digital source images comprises one or more normalized digital source images, and wherein the synthesizing or selecting of the first representative image includes synthesizing or selecting from the one or more normalized digital source images.

24. The non-transitory computer-readable medium of claim 23, wherein the one or more normalized digital source images are normalized using one or more of the following:
  performing noise reduction;
  adjusting orientation;
  cropping;
  adjusting brightness; or
  adjusting contrast.

* * * * *